(12) United States Patent
Huang et al.

(10) Patent No.: US 7,402,801 B2
(45) Date of Patent: Jul. 22, 2008

(54) INSPECTING METHOD OF A DEFECT INSPECTION DEVICE

(75) Inventors: Henry Huang, Hsinchu (TW); YongSeng Tan, Hsinchu (TW)

(73) Assignee: UMCi Ltd, Singapore (SG)

( * ) Notice: Subject to any disclaimer, the term of this patent is extended or adjusted under 35 U.S.C. 154(b) by 344 days.

(21) Appl. No.: 10/907,678

(22) Filed: Apr. 12, 2005

(65) Prior Publication Data
US 2006/0226356 A1   Oct. 12, 2006

(51) Int. Cl.
*H01L 21/00*   (2006.01)
(52) U.S. Cl. ............................. 250/307; 438/5; 438/10; 438/11
(58) Field of Classification Search .................. None
See application file for complete search history.

(56) References Cited

U.S. PATENT DOCUMENTS 6,451,185 B2    9/2002    Beier et al. ............. 204/298.12
6,967,110 B2 *  11/2005   Guldi et al. ................... 438/11

FOREIGN PATENT DOCUMENTS

CN          1355558         6/2002

* cited by examiner

*Primary Examiner*—David A. Vanore
(74) *Attorney, Agent, or Firm*—Jianq Chyun IP Office

(57) ABSTRACT

An inspecting method comprises the following steps. A plurality of defect inspection devices is formed on a wafer. Each defect inspection device comprises an insulating layer and a conductive layer stacked over the insulating layer. A defect inspection parameter is set and the wafer is scanned with an electron beam to obtain a plurality of defect signals. The number of defect signals is checked to determine if it is equal to the number of defect inspection devices. If the number of defect signals is smaller than the number of defect inspection devices, the defect inspection parameter is readjusted and the aforementioned step of performing an electron beam scanning and checking for equality between the number of defect signals and the number of defect inspection devices are repeated. The process is complete when the number of defect signals is at least equal to the number of defect inspection devices.

5 Claims, 8 Drawing Sheets

INSPECTING METHOD OF A DEFECT INSPECTION DEVICE

BACKGROUND OF THE INVENTION

1. Field of the Invention

The present invention relates to a defect inspection device and an inspecting method thereof. More particularly, the present invention relates to a defect inspection device and an inspecting method thereof with using an electron beam.

2. Description of the Related Art

With the continuous research in the technique of fabricating ultra large scale integrated circuits, the level of integration of integrated circuits on a wafer increases many folds. As circuits and devices are miniaturized, very small manufacturing defects have become a significant factor affecting overall quality of the product. In the past decade, defect inspection for detecting manufacturing defects has become a part of the standard manufacturing procedure. Typically, defect inspection is a statistical sampling procedure that applies to defect prone or defect sensitive manufacturing steps.

The conventional method of detecting defects on a wafer is basically a trial and error method. First, a defect inspection parameter is set and a wafer scanning is carried out. According to the defect signal, the operator singles out and opens up the defective device to perform an inspection to confirm if the device is really a defective device. If the device is really defective, the defect inspection parameter can be used to inspect the same batch of wafers. If the device is found not to be defective, the defect inspection parameter is reset and another inspection is performed until a device returning a defect signal is actually defective. Although the aforementioned trial and error method of finding the inspection parameter is effective, the procedure is long and tedious.

In another inspection method disclosed in U.S. Pat. No. 6,451,185 B1, an optical inspection device is used to detect purposely laid defective elements on a wafer so that a suitable defect inspection parameter is obtained. The parameter is then applied to perform a subsequent inspection. However, the defective elements purposely laid on the wafer are subjected to certain character restrictions imposed by defect detection with an optical inspection device. For example, the defective element must have a reflective upper surface so that the type of material that can be used for forming the defective element is limited. Furthermore, the need to fabricate these defective elements increases the complexity of fabricating the original wafer.

SUMMARY OF THE INVENTION

Accordingly, at least one objective of the present invention is to provide an inspection method for defect inspection device capable of shortening the defect inspection cycle.

At least a second objective of the present invention is to provide a method of manufacturing a defect inspection device such that the fabrication of the defect inspection device merges within the normal fabricating steps and hence simplifies the fabrication of the defect inspection device considerably.

At least a third objective of the present invention is to provide another method of manufacturing a defect inspection device such that the fabrication of the defect inspection device merges within the normal fabricating steps and hence simplifies the fabrication of the defect inspection device considerably.

At least a fourth objective of the present invention is to provide a defect inspection device structure that facilitates a speedy and accurate inspection of the defect device.

At least a fifth objective of the present invention is to provide another defect inspection device structure that facilitates a speedy and accurate inspection of the defect device.

To achieve these and other advantages and in accordance with the purpose of the invention, as embodied and broadly described herein, the invention provides an inspection method for defect inspection device comprising the following steps. First, a plurality of defect inspection devices is formed on a wafer. Each defect inspection device comprises an insulating layer and a conductive layer stacked over the insulating layer. A defect inspection parameter is set and then the wafer is scanned with an electron beam to obtain a plurality of defect signals. The number of defect signals is checked to determine if it is equal to the number of defect inspection devices. If the number of defect signals is smaller than the number of defect inspection devices, the defect inspection parameter is readjusted and the aforementioned step of performing an electron beam scanning and checking for equality between the number of defect signals and the number of defect inspection devices are repeated. The process is complete when the number of defect signals is at least equal to the number of defect inspection devices.

The present invention also provides a method of fabricating defect inspection devices. First, a plurality of conductive structures is formed on a wafer. Next, a spacer material layer is formed over the wafer to cover the conductive structures. Thereafter, a portion of the spacer material layer is removed to form spacers on the sidewalls of the conductive structures and retaining the spacer material layer between the sidewall spacers of two adjacent conductive structures. After that, an insulating layer is formed over the wafer to cover the conductive structures. The insulating layer has a plurality of defect contact openings that expose the spacer material layer. Finally, conductive material is deposited into various defect contact openings.

The present invention also provides a second method of fabricating defect inspection devices. First, a wafer having a plurality of scribe lines defining out a plurality of chips is provided. Next, a first insulating layer and a conductive layer are sequentially formed over the wafer. Thereafter, the first insulating layer and the conductive layer are patterned to form a plurality of conductive stack structures on the chip regions and a plurality of defect stack structures for detecting defects on the scribe lines. After that, a second insulating layer is formed over the wafer to cover the conductive stack structures and the defect stack structures. Furthermore, the second insulating layer has at least a plurality of defect contact openings that expose the defect stack structures. Finally, conductive material is deposited into the defect contact openings.

The present invention also provides a defect inspection device structure. The defect inspection device comprises a substrate, a plurality of defect contacts, a plurality of spacers and an insulating layer. The substrate comprises a plurality of conductive structures. Each defect contact is disposed between a pair of neighboring conductive structures. The spacers are disposed between the defect contacts and various conductive structures. The insulating layer is disposed between the defect contacts and the substrate.

The present invention also provides a second defect inspection device structure. The defect inspection device comprises a first insulating layer, a conductive layer, a second insulating layer and a plurality of defect contacts. The first insulating layer is disposed on the scribe lines of a wafer and the conductive layer is disposed over the first insulating layer. The second insulating layer covers the conductive layer and the substrate. The defect contacts are disposed in the second insulating layer above the conductive layer.

In the inspection method of the present invention, a plurality of purposely fabricated defect inspection devices on a wafer is scanned with an electron beam to determine the defect inspection parameter necessary for inspecting the defects on a wafer. Therefore, the inspection method of the present invention is simpler and faster than the conventional one so that time and cost spent on defect detection can be reduced. In addition, the defect inspection devices can be fabricated using a conventional method. In other words, the same processing steps can be used to form the defect inspection devices as well as ordinary devices so that both can be carried out concurrently to save processing steps.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE PREFERRED EMBODIMENTS

Figure 1:
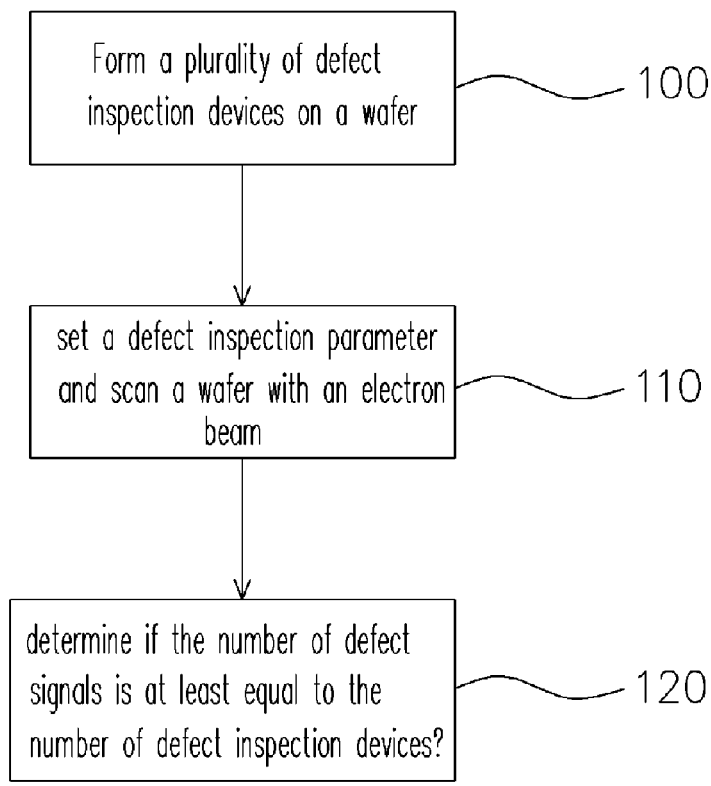
FIG. 1 is a flowchart showing the steps for inspecting the defect inspection device on a wafer according to one preferred embodiment of the present invention.

Reference will now be made in detail to the present preferred embodiments of the invention, examples of which are illustrated in the accompanying drawings. Wherever possible, the same reference numbers are used in the drawings and the description to refer to the same or like parts.

FIG. 1 is a flowchart showing the steps for inspecting the defect inspection device on a wafer according to one preferred embodiment of the present invention. The inspection method of the present invention comprises forming a plurality of defect inspection devices on a wafer (in step 100). Each defect inspection device comprises an insulating layer and a conductive layer stacked on the insulating layer.

Figure 2:
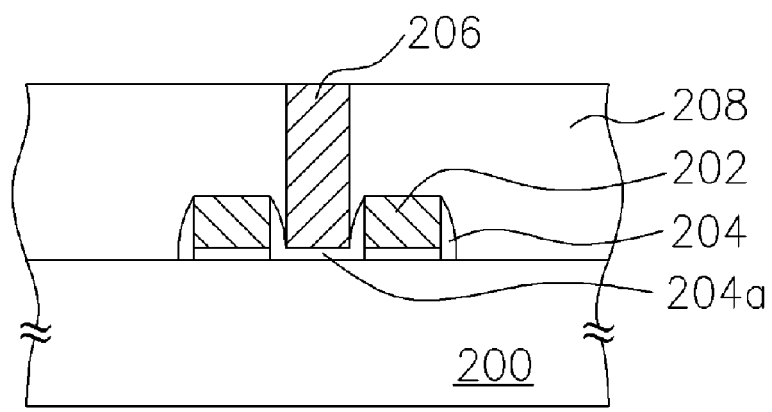
FIG. 2 is a schematic cross-sectional view of a defect inspection device structure according to one preferred embodiment of the present invention.
Figure 5:
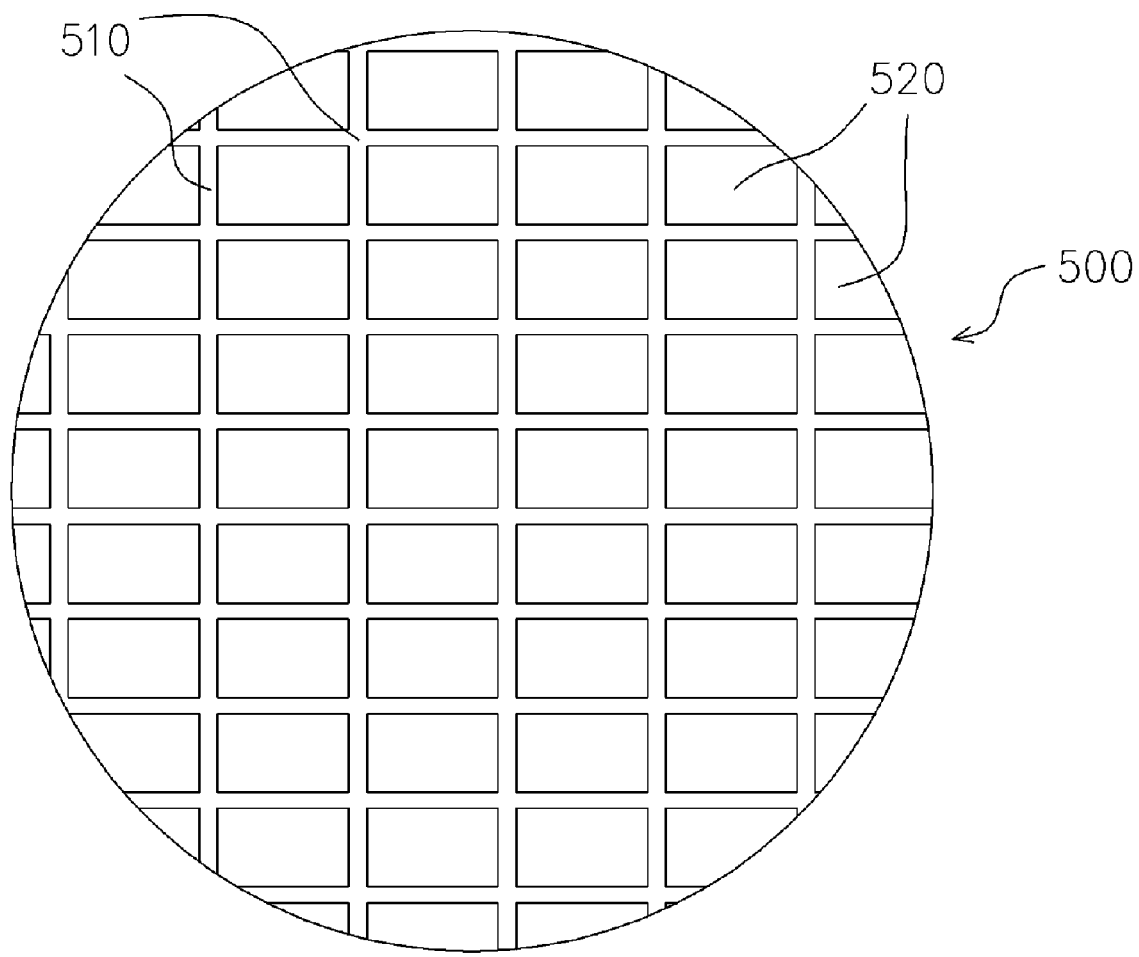
FIG. 5 is a top view of a wafer according to one embodiment of the present invention.

In one preferred embodiment, the defect inspection device has a structure as shown in FIG. 2. The defect inspection device is disposed on a chip region within the wafer (520 as shown in FIG. 5). The defect inspection device comprises a substrate 200, a defect contact 206, spacers 204 and an insulating layer 204a. In fact, the substrate 200 is the wafer. Furthermore, the substrate 200 has a plurality of conductive structures 202 thereon. The defect contact 206 is disposed between a pair of neighboring conductive structures 202. The defect contact 206 is fabricated using a conductive material, for example. In addition, the spacers 204 are disposed between the defect contact 206 and the conductive structures 202. The insulating layer 204a is disposed between the defect contact 206 and the substrate 200. In one preferred embodiment, the spacers 204 and the insulating layer 204a are fabricated using the same material. In another preferred embodiment, the defect inspection device structure further comprise an insulating layer 208 that covers the substrate 200 and the conductive structures 202 and encloses the defect contact 206.

Figure 3A:
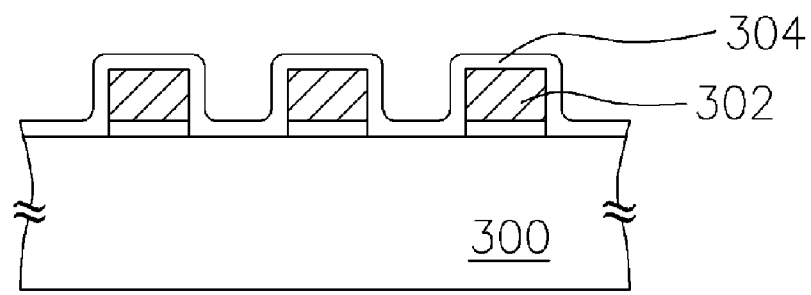
FIGS. 3A through 3D are schematic cross-sectional views showing the steps for fabricating a defect inspection device according to one preferred embodiment of the present invention.

The defect inspection device shown in FIG. 2 is fabricated in the same processing steps necessary for forming contacts for linking with ordinary devices as shown in FIGS. 3A through 3D. First, as shown in FIG. 3A, a plurality of conductive structures 302 is formed on a wafer 300. The conductive structure 302 can be a metal-oxide-semiconductor (MOS) device, for example. Thereafter, a spacer material layer 304 is formed over the wafer 300 to cover the conductive structures 302. The spacer material layer 304 is a silicon nitride layer formed, for example, by performing a chemical vapor deposition (CVD) process.

Figure 3B:
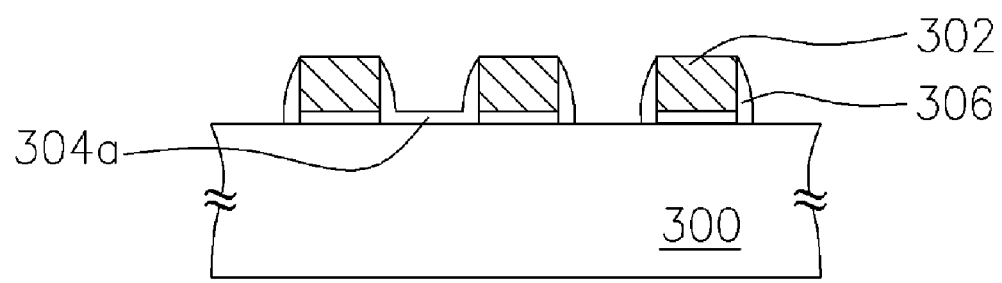

As shown in FIG. 3B, a portion of the spacer material layer 304 is removed to form spacers 306 on the sidewalls of the conductive structure 302 and retaining a spacer material layer 304a between a pair of neighboring conductive structures 302. The areas where the spacer material layer 304a is retained are the locations for forming defect contacts in a subsequent operation and the areas where the spacer material layer 304 is removed are the locations for forming contacts.

The method of removing a portion of the spacer material 304, for example, comprises the following steps. First, a photoresist layer (not shown) is spin-coated over the spacer material layer 304. A photolithographic process is carried out to form a patterned photoresist layer over the region between a pair of neighboring conductive structures 302 designed to form the defect contacts. Thereafter, an etching step is carried out to remove a portion of the spacer material layer 304 to form spacers 306 on the sidewalls of the conductive structures 302 and the spacer material layer 304a. Finally, the photoresist layer is removed.

Figure 3C:
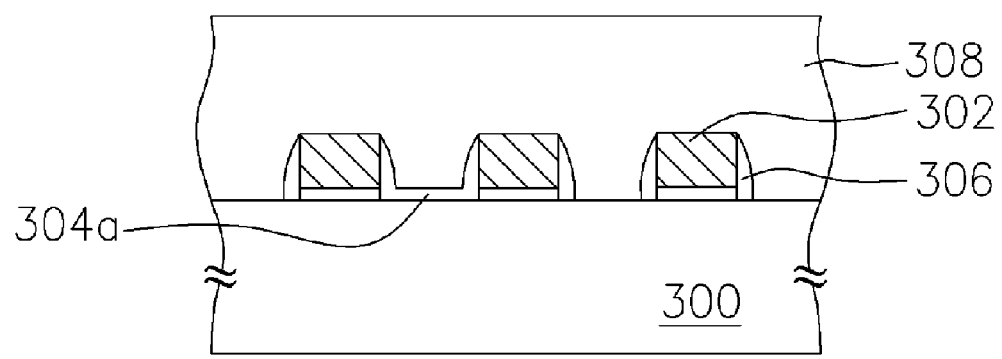

As shown in FIG. 3C, an insulating layer 308 is formed over the wafer 300. The insulating layer 308 is a dielectric layer such as a silicon oxide layer, a silicon nitride layer or a silicon oxynitride layer formed, for example, by performing a chemical vapor deposition process.

Figure 3D:
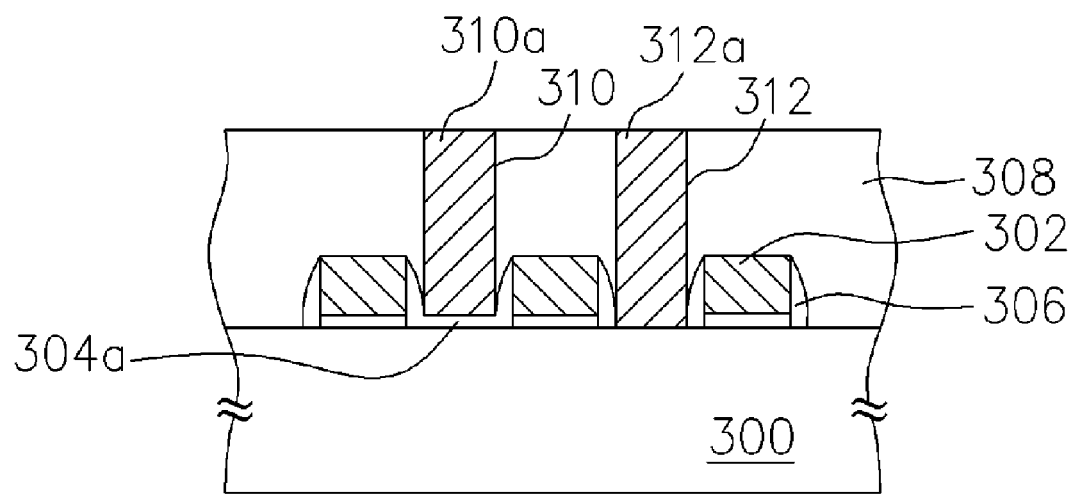

As shown in FIG. 3D, a defect contact opening 310 and a contact opening 312 are formed in the insulating layer 308. The defect contact opening 310 exposes the spacer material layer 304a. The method of forming the defect contact openings 310 and the contact opening 312 includes, for example, performing a photolithographic and etching process to form openings between the conductive structures 302.

Thereafter, conductive material is deposited into the defect contact openings 310 and the contact opening 312 to form a defect contact 310a and a contact 312a. The conductive material can be a metal such as tungsten, aluminum or copper or an alloy such as tungsten silicide. The defect contact 310a and the contact 312a are formed, for example, by depositing a conductive material over the insulating layer 308 to fill the defect contact opening 310 and the contact opening 312 and removing the conductive material outside the defect contact opening 310 and the contact opening 312.

Because the defect inspection devices of the present invention can be fabricated in the same steps for forming other devices, considerable production cost is saved.

Figure 4:
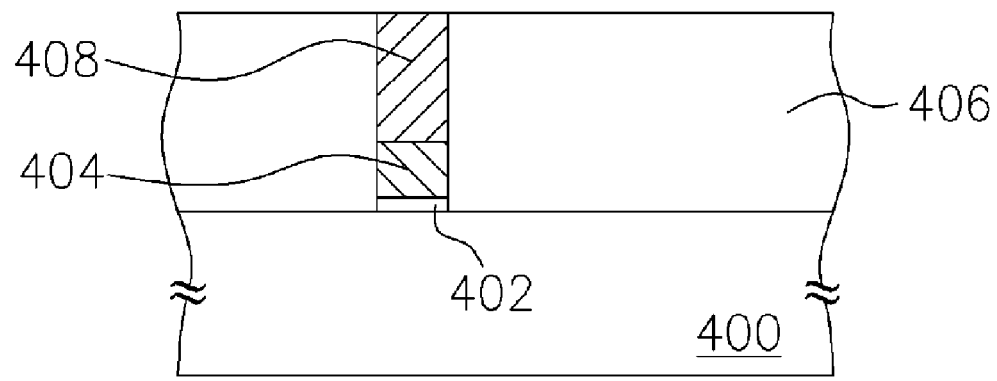
FIG. 4 is a schematic cross-sectional view of a defect inspection device structure according to another preferred embodiment of the present invention.

In another preferred embodiment, the defect inspection device has a structure shown in FIG. 4. The defect inspection device is located on the scribe lines (510 in FIG. 5) of a wafer. The defect inspection device comprises an insulating layer 402, a conductive layer 404, a second insulating layer 406 and a defect contact 408. The insulating layer 402 is disposed over the substrate 400 (the scribe line of the wafer) and the conductive layer 404 is disposed over the insulating layer 402. The insulating layer 406 covers the conductive layer 404 and the substrate 400. The defect contact 408 is disposed in the insulating layer 406 above the conductive layer 404. The defect contact 408 is fabricated from a conductive material.

Figure 6A:
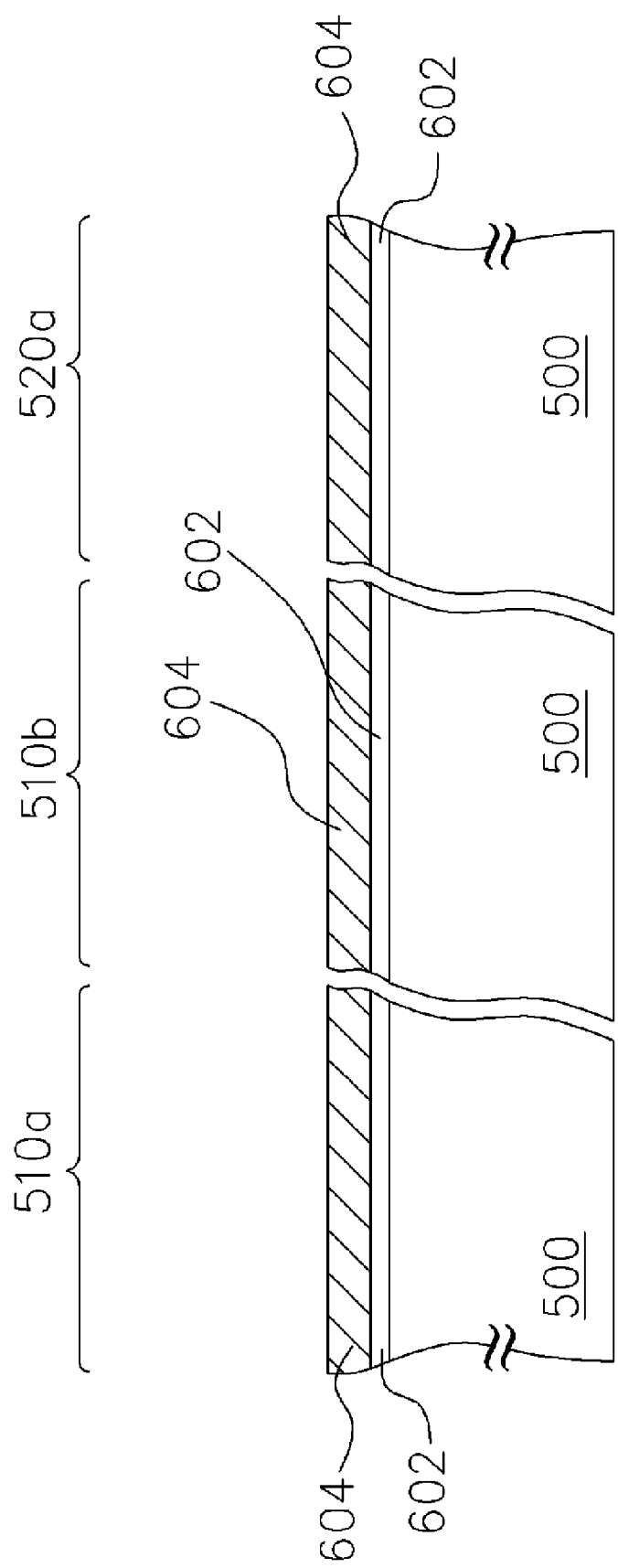
FIGS. 6A through 6C are schematic cross-sectional views showing the steps for fabricating a defect inspection device according to another preferred embodiment of the present invention.
Figure 6B:
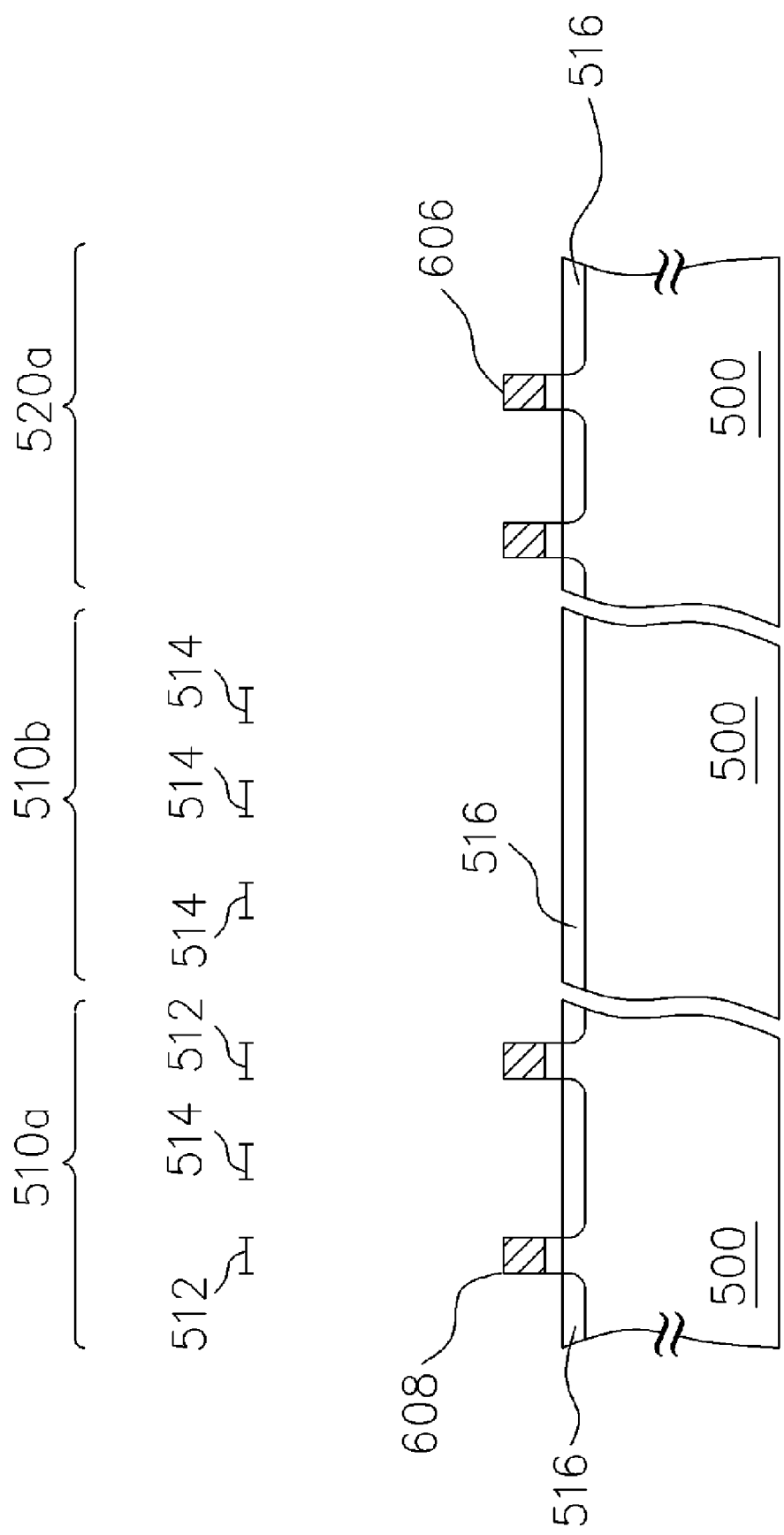
Figure 6C:
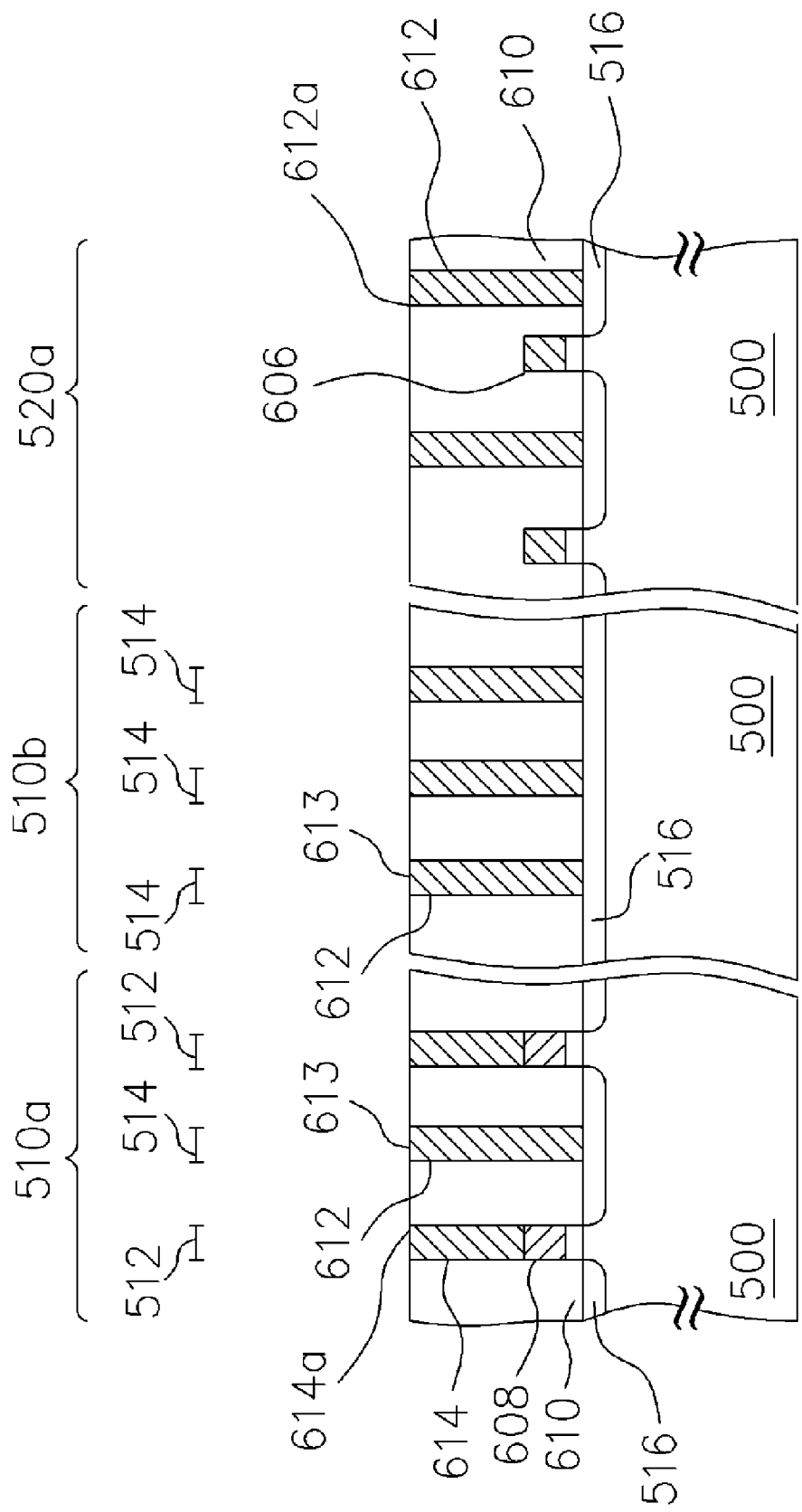

The defect inspection device shown in FIG. 4 is formed in the same processing steps for forming contacts for linking ordinary devices or test keys on the scribe lines as shown in FIGS. 6A through 6C. As shown in FIGS. 5 and 6A, a wafer 500 is provided. The wafer has a plurality of scribe lines 510 for defining a plurality of chips 520 formed thereon. Thereafter, an insulating layer 602 and a conductive layer 604 are formed over the scribe lines 510a, 510b and the chip regions 520a of the wafer 500. The insulating layer 602 is a silicon oxide layer formed in a thermal oxidation process and the conductive layer 604 is a polysilicon layer formed in a chemical vapor deposition process, for example.

As shown in FIG. 6B, the insulating layer 602 and the conductive layer 604 are patterned to form a plurality of conductive stack structures 606 on the chip regions 520a and a plurality of defect stack structures 608 on the scribe lines 510a in a region 512 designated for forming the test key. However, no defect stack structures are formed on other test key positions 514 on the scribe lines 510a and 510b. The method of forming the conductive stack structure 606 and the defect stack structure 608 includes performing a photolithographic and etching process for the insulating layer 602 and the conductive layer 604, for example. Thereafter, using the conductive stack structure 606 and the defect stack structure 608 as a mask, an ion implantation is carried out to form a doped region 516 in the wafer 500.

As shown in FIG. 6C, an insulating layer 610 is formed over the wafer 500 to cover the conductive stack structure 606, the defect stack structure 608 and the wafer 500. The insulation layer 610 is a silicon oxide layer formed in a chemical vapor deposition process, for example.

Thereafter, a plurality of contact openings 612 and a plurality of defect contact openings 614 are formed in the insulating layer 610. The contact openings 612 are disposed on the chip regions of the wafer 500 and other positions 514 designated to form the test keys. The defect contact openings 614 are disposed on the designated locations 512 for forming the defect contacts. In other words, the defect contact openings 614 are formed on the defect stack structure 608.

After that, conductive material is deposited into the openings to form contacts 612a in the chip region 520a and test keys 613 and defect contacts in the scribe line regions 510a and 510b. The conductive material is a metal such as copper, aluminum or tungsten. The contacts 612a, the test keys 613 and the defect contacts 614a are formed, for example, by depositing conductive material over the insulating layer 610 to fill the contact openings 612 and the defect contact openings 614 and removing any excess conductive material outside the openings.

As shown in FIG. 1, the second step 110 in the inspecting method is to set up a defect inspection parameter and scan the wafer with an electron beam to obtain a plurality of scan signals. Through a defect inspection device, the difference between the conductive devices and the defect inspection devices on the wafer is analyzed to detect the defect signals. The inspection method includes using an electron beam to serve as a probing source. When the electron beam bombards the inspection device, secondary electrons are emitted from the inspection device. For example, if an electron beam targets a conductive structure, secondary electrons indicating a close state are emitted. On the other hand, if an electron beam targets a defect inspection device, second electrons indicating an open state are emitted. Thereafter, through an image-processing system, a bright spot is produced in the locations where the quantity of the secondary electrons emitted is high and a dark spot is produce in the locations where the quantity of secondary electrons emitted is low. According to the brightness contrast in the image, the distribution of the conductive structures and the defect inspection device can be determined.

Figure 7:
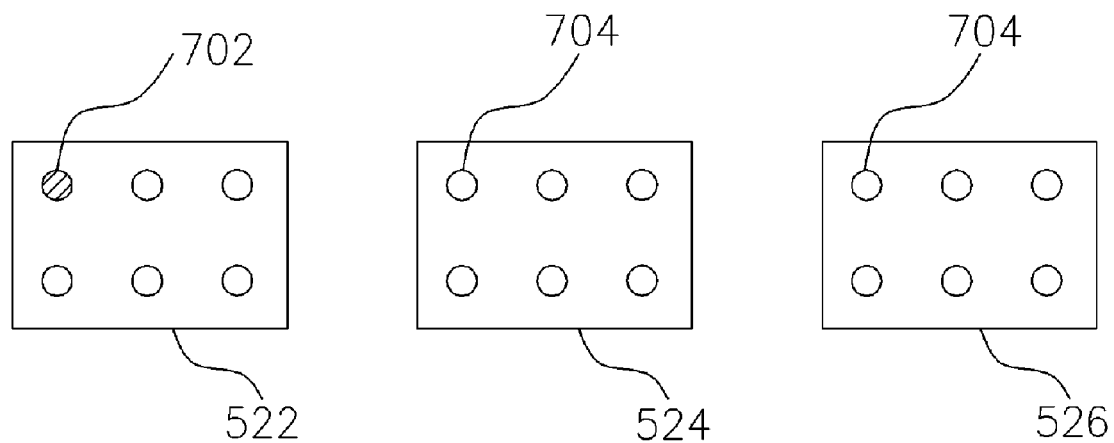
FIG. 7 is a top view showing a plurality of devices within the chip regions according to the present invention.

In the following, the defect structure shown in FIG. 3D is used as an example. As shown in FIGS. 3D, 5 and 7, the wafer 500 has a plurality of chips 520 and one of the chip regions 522 has at least a defect inspection device 702. The defect inspection device 702 is a defect contact 310a (as shown in FIG. 3D) and FIG. 7 shows a top view of it. In addition, conductive devices 704 are formed in corresponding positions on other chip regions such as 524 and 526. The conductive devices 704 are contacts 312a (as shown in FIG. 3D) and FIG. 7 shows a top view of it. When an electron beam scans over the conductive device 704, secondary electrons indicating a close state are produced. On the contrary, when the electron beam scans over the defect inspection device 702, secondary electrons indicating an open state are produced. By comparing the signals with the scan signals obtained from one having conductive devices 704 and defect inspection device 702 in corresponding locations, defects can be readily determined through any difference in image contrast.

Figure 8:
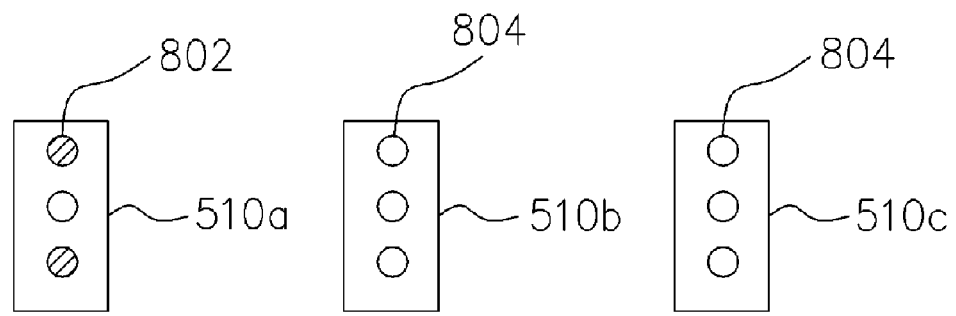
FIG. 8 is a top view showing a plurality of devices within the scribe line regions according to the present invention.

In addition, another type of inspection can be illustrated using the defect inspection device as shown in FIG. 6C. As shown in FIGS. 5, 6C and 8, the wafer 500 has a plurality of scribe lines 510 and at least a defect inspection device 802 is formed in one of the scribe line regions 510a. The defect inspection device 802 is a defect contact 614a (as shown in FIG. 6C) and FIG. 8 is a top view of it. Furthermore, conductive devices 804 are formed in corresponding positions on other scribe line regions such as 510b and 510c. The conductive devices 804 are test keys 613 (as shown in FIG. 6C) and FIG. 8 is a top view it. When an electron beam scans over the conductive device 804, secondary electrons indicating a close state are produced. On the contrary, when the electron beam scans over the defect inspection device 802, secondary electrons indicating an open state are produced. By comparing the signals with the scan signals obtained from one having conductive devices 804 and defect inspection device 802 in corresponding locations, defects can be readily determined through any difference in image contrast.

As shown in FIG. 1, the third step 120 in the inspecting method is to determine if the number of defect signals is at least equal to the number of defect inspection device. If the number of defect signals is smaller than the defect inspection devices, the defect inspection parameter is readjusted and the actions indicated in steps 110 and 120 are repeated until the number of defect signals and the number of defect inspection devices are equal. When the number of defect signals is at least equal to the number of defect inspection device, the defect inspection parameter is a suitable parameter to use in the defect inspection device for carrying out the inspection because the inspection will not over or under response to defects. Hence, the defect inspection parameter thus discovered can be directly used in subsequent wafer inspection.

In summary, the inspection method of the present invention utilizes an electron beam to scan the defect inspection devices on a wafer and obtains a suitable defect inspection parameter. This method can rapidly find the optimal defect inspection parameter so that the time needed to inspect a wafer for defects is shortened. Hence, overall production yield is increased. Furthermore, the defect inspection device used for carrying out the defect inspection can be fabricated in conventional fabricating steps for forming other devices. Thus, considerable labor and processing steps are saved.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. An inspecting method for defect inspection device, comprising the steps of:

forming a plurality of defect inspection devices on a wafer, wherein each defect inspection device comprises an insulating layer and a conductive layer stacked on the insulating layer;

setting a defect inspection parameter and scanning the wafer with an electron beam to obtain a plurality of defect signals; and determining whether the number of defect signals is at least equal to the number of defect inspection devices, if the number of defect signals is smaller than the number of defect inspection devices, then readjust the defect inspection parameter and repeat the steps of setting the defect inspection parameter, scanning the wafer with electron beam and determining the equality between the number of defect signals and the number of defect inspection devices until the number of defect signals is at least equal to the number of defect inspection devices.

2. The inspecting method of claim 1, wherein the step of forming the defect inspection devices further comprises forming a plurality of conductive devices on the wafer, and in the process of scanning with an electron beam, comparing the scan signal from the conductive device with the scan signal from the defect inspection device.

3. The inspecting method of claim 2, wherein the wafer has a plurality of chips with one of the chips having at least a defect inspection device while the other chips having a conductive device in a corresponding position, and in the process of scanning with an electron beam, the scan signal from the conductive device is compared with the scan signal from the corresponding defect inspection device.

4. The inspecting method of claim 2, wherein the wafer has a plurality of scribe lines with the position on one of the scribe lines for forming a test key having at least a defect inspection device while a test key is formed in a corresponding position on the other scribe lines, and in the process of scanning with an electron beam, the scan signal from the defect inspection device is compared with the scan signal from a corresponding test key.

5. The inspecting method of claim 2, wherein the scan signals are secondary electron emissions from the conductive device or the defect inspection device.

* * * * *